United States Patent

Rounbehler et al.

Patent Number: 6,057,162
Date of Patent: May 2, 2000

[54] DISEASE DIAGNOSIS BY VAPOR SAMPLE ANALYSIS

[75] Inventors: David P. Rounbehler, Chelmsford; David B. Wheeler, Lunenburg; David H. Fine, Lincoln; George B. Jarvis, Arlington, all of Mass.

[73] Assignee: Thermedics Detection, Inc., Chelmsford, Mass.

[21] Appl. No.: 08/928,735

[22] Filed: Sep. 12, 1997

Related U.S. Application Data

[63] Continuation-in-part of application No. 08/813,497, Mar. 7, 1997, abandoned, which is a continuation of application No. 08/399,603, Mar. 7, 1998, abandoned.

[51] Int. Cl.[7] ............................................... G01N 33/00
[52] U.S. Cl. ..................... 436/119; 436/120; 436/135; 436/172; 73/23.2; 422/83
[58] Field of Search .................................. 436/119, 120, 436/121, 122, 135, 139, 172, 900; 422/52, 82.05, 82.08, 83, 84, 89, 98; 73/23.2, 23.34; 600/532

[56] References Cited

U.S. PATENT DOCUMENTS

| | | | |
|---|---|---|---|
| 3,655,302 | 4/1972 | Lees et al. | 418/61.2 |
| 3,763,877 | 10/1973 | Lieb | 137/115.09 |
| 3,771,351 | 11/1973 | Sacks et al. | 73/52 |
| 3,845,309 | 10/1974 | Helm et al. | 250/365 |
| 3,973,910 | 8/1976 | Fine | 436/107 |
| 3,996,002 | 12/1976 | Fine | 436/107 |
| 4,119,089 | 10/1978 | Preti et al. | 436/65 |
| 4,285,697 | 8/1981 | Neary | 436/20 |
| 4,349,626 | 9/1982 | Labows et al. | 435/38 |
| 4,563,893 | 1/1986 | Tanyolac et al. | 73/23.34 |
| 4,678,756 | 7/1987 | Parks | 436/123 |
| 4,772,559 | 9/1988 | Preti et al. | 436/64 |
| 4,775,633 | 10/1988 | Rounbehler | 436/106 |
| 5,042,501 | 8/1991 | Kenny et al. | 600/532 |
| 5,199,575 | 4/1993 | McHugh | 209/522 |
| 5,227,135 | 7/1993 | Godec et al. | 422/98 |
| 5,310,683 | 5/1994 | Godec et al. | 436/123 |
| 5,318,911 | 6/1994 | Fine et al. | 436/47 |
| 5,330,714 | 7/1994 | Godec et al. | 422/52 |
| 5,352,611 | 10/1994 | Fine et al. | 436/43 |
| 5,397,540 | 3/1995 | Rounbehler et al. | 422/82.08 |
| 5,424,217 | 6/1995 | Benner et al. | 436/123 |
| 5,501,981 | 3/1996 | Ray et al. | 436/123 |
| 5,614,417 | 3/1997 | Kubala et al. | 436/120 |
| 5,661,036 | 8/1997 | Benner et al. | 436/123 |

FOREIGN PATENT DOCUMENTS

| | | |
|---|---|---|
| WO 94/10563 | 5/1994 | WIPO. |
| WO 94/20835 | 9/1994 | WIPO. |
| WO 95/22049 | 8/1995 | WIPO. |

OTHER PUBLICATIONS

Adewuyi, Yusuf G., "Oxidation of Biogenic Sulfur Compounds in Aqueous Media," *Biogenic Sulfur in the Environment*, Saltzman, et al., Eds., Chapter 34, American Chemical Society, Washington, D.C., 1989.

"Flavor," Analytical Chemistry, vol. 65, No. 12, Jun. 15, 1993, pp. 343R–345R; 358R–359R.

"Intelligent Sensor Technology," published by Aroma Scan, with attached Price List dated Jul. 1, 1994.

Benner, Richard L., et al., "Universal Sulfur Detection by Chemiluminescence," Analytical Chemistry, vol. 61, No. 11, Jun. 1, 1989, pp. 1268–1271.

Fessenden, Ralph J., et al., *Organic Chemistry*, Chapter 18, "Amino Acids and Proteins," Willard Grant Press, 1979, Boston, Massachusetts, pp. 834–835.

Frobisher, Jr., Martin, *Fundamentals of Bacteriology*, Fourth Edition, Illustrated, W.B. Saunders Company, Philadelphia and London, 1949, pp. 134: 137–142; 289–305; 643–647; 649–663; 701.

(List continued on next page.)

*Primary Examiner*—Maureen M. Wallenhorst
*Attorney, Agent, or Firm*—Ernest V. Linek; Banner & Witcoff, Ltd.

[57] ABSTRACT

Diagnosing disease in a body by analyzing a sample from the body for the presence of sulfur compounds.

20 Claims, 7 Drawing Sheets

OTHER PUBLICATIONS

Intrapichet, Kanok–Orn, et al., "Volatile Compounds Produced by Meat Pseudomonas Grown on Beef at Refrigeration Temperatures," ASEAN Food Journal, vol. 8, No. 1, 1993, pp. 14–21.

Jollivet, Nathalie, et al., "Production of Volatile Compounds in Liquid Cultures by Six Strains of Coryneform Bacteria," Appl Microbiol Biotechnol, vol. 36, Springer–Verlag, 1992, pp. 790–794.

Josephson, David B., et al., "Measurement of Volatile Aroma Constituents as a Means for Following Sensory Deterioration of Fresh Fish and Fishery Products," *Seafood Quality Determination*, Kramer, Donald E., et al., Eds., Proceedings of International Symposium on Seafood Quality Determination, Univ. of Alaska, Nov. 10–14, 1986, pp. 27–45.

Luong, J.H.T., et al., "Development of a Fish Freshness Sensor," Reprinted from *American Biotechnology Laboratory*, Nov. 1988.

"Is it Fresh! Microfresh Will Tell You," Pegasus Biotechnology, Ontario, Canada, including letter dated May 9, 1994.

Plane, John M. C., "Gas–Phase Atmospheric Oxidation of Biogenic Sulfur Compounds," *Biogenic Sulfur in the Environment*, Saltzman, et al., Eds., Chapter 24, American Chemical Society, Washington, D.C., 1989.

Prescott, Lansing m., et al., *Microbiology*, Chapter 43, "Microbiology of Food," Wm. C. Brown Publishers, Dubuque, Iowa, 1990, pp. 840–858.

Taylor, Barrie F., et al., "Microbial Metabolism of Dimethyl Sulfide," *Biogenic Sulfur in the Environment*, Saltzman, et al., Eds., Chapter 13, American Chemical Society, Washington, D.C., 1989.

Tyndall, G. S., et al., "Atmospheric Reactions of $CH_3S$ Radicals," *Biogenic Sulfur in the Environment*, Saltzman, et al., Eds., Chapter 27, American Chemical Society, Washington, D.C., 1989.

*Protocol*—United States Tuna Foundation, Washington, D.C., Aug. 23, 1993, pp. 1–8.

Strachan et al., International Journal of Food Science & Technology, vol. 27, 1992, pp. 261–269.

Kamiya et al., Journal of Chromatography, vol. 292, 1984, pp. 383–391.

Thampuran et al., Fishery Technology, vol. 27, No. 2., 1990, pp. 145–150.

Xu, Xiaoyong et al., "Examination of Sulfur Forms in Coal by Direct Pyrolysis and Chemlumin Essence Detection," FUEL, vol. 74, No. 10, 1995, pp. 1499–1504.

DISEASE DIAGNOSIS BY VAPOR SAMPLE ANALYSIS

CROSS REFERENCE TO RELATED APPLICATIONS

This application is a continuation-in-part of U.S. Ser. No. 08/813,497, filed Mar. 7, 1997, now abandoned, the entire contents of which is incorporated herein by reference, which is a continuation of U.S. application Ser. No. 08/399,603, filed Mar. 7, 1998, now abandoned.

FIELD OF THE INVENTION

This invention relates to disease diagnosis by vapor sample analysis.

BACKGROUND

Vapor samples are analyzed from biological sources for various purposes. For example, breath samples are taken and analyzed to determine whether the subject has recently consumed alcoholic beverages or to diagnose certain diseases.

Sulfur compounds have been detected by chemiluminescence reaction with ozone. A typical technique, used, for example, in the bottle industry, involves burning the sample in the presence of a metal catalyst and a reducing agent, such as hydrogen, to produce $H_2S$ or SO. These compounds are reacted with ozone to produce $SO_2$ which is luminescent and can thus be detected.

Gas chromatography is a technique in which a mixture of unknown chemical compounds is carried by a flow of inert gas through a column that has been coated with a polymer. The chemical compounds become separated spatially along the column because of their differing affinities for the column of polymer. Generally, higher molecular weight, less volatile compounds are retained to a greater extent than lower molecular weight, more volatile compounds. The compounds emerge from the column in sequence and can be detected and identified. To optimize the analysis, the polymer material can be selected for retention of different types of compounds. The temperature of the column can also be varied during the analysis.

SUMMARY OF THE INVENTION

The invention relates to diagnosing disease, such as cancer, by analyzing a vapor sample from a biological source, such as a living animal.

In an aspect, the invention features a system and method of assisting diagnoses of disease in biological matter. A vapor sample is obtained from the biological matter. The vapor sample is analyzed for the presence of sulfur compounds in a concentration range of about 500 femtograms or less. An analyzer responsive to the detector is provided for assisting diagnoses of disease.

In another aspect, the invention features assisting diagnoses of disease in biological matter including obtaining a vapor sample from the biological matter, analyzing the vapor sample for the presence of sulfur compounds without added sulfur compound-inducing treatment, and assisting diagnoses of disease based on the analyzing. In embodiments, the aspects may include vapor sample analyzing by luminescent reaction with ozone.

In yet another aspect, the invention features assisting diagnoses of disease in biological matter including obtaining a vapor sample from the biological matter, analyzing the vapor sample by luminescent reaction with ozone for the presence of sulfur compounds, and assisting diagnoses of disease based on the analyzing.

Embodiments may include one or more of the following features. The vapor sample may be a breath sample. The vapor sample may be exposed to ozone at a pressure from about 0.5 atm to about 3 atm during the analysis. The vapor sample may be exposed to a heated metal prior to luminescent reaction with ozone. The metal may be heated to a temperature from about 200° C. to about 500° C. The vapor sample may be exposed to the metal without the presence of added reducing agent. The sample may be processed by gas chromatography. Diagnosis of the presence or absence of the disease may be based on the profile (e.g., the absence or presence or the concentration ratio) of particular sulfur compounds may be reported. The presence or absence of the disease may be based on the profile of volatile sulfur compounds (having a vapor pressure of 1 mm Hg at room temperature) such as dimethyl sulfide, methyl mercaptan, hydrogen sulfide, dimethyl disulfide or sulfur dioxide.

The following features may also be included: The disease may be cancer or precancer, liver disease, internal infections, ulcers, bacterial infections, viral infections or heart disease. The sulfur compounds may be detected in a concentration range of about 500 femtograms or less, preferably, in a range of about 25 femtograms or less. The sulfur compounds may be quantified.

Embodiments of the invention may provide one or more advantages. For example, high sensitivity analysis of sulfur compounds can provide advantages in the types of diseases or stage at which diseases can be detected, the types of biological matter from which samples can be taken, and the ease and speed of the analysis. For example, diseases, such as cancer or precancer may be detected at an early stage when treatment may still be effective. Analysis may also be useful in research relating to the detection and treatment of disease. The sample may be obtained, e.g., from breath, skin outgassing, urine or feces, often without pretreatment, e.g., concentrating, to the sample. Sulfur compounds from biological sources can be detected with high sensitivity, e.g. in the femtogram range, e.g., 500 femtograms or less, such as 25 femtograms. Sampling may be conducted quickly, with little discomfort. Alternatively, disease may be detected rapidly and easily port-mortem. The detection may be accomplished without using a sulfur compound-enhancing treatment such as preconcentration of the sample or a dietary supplement supplied to the patient. Analysis of samples in vapor form is convenient and fast compared to wet chemical analysis and treatment.

Still other aspects, features, and advantages follow.

DESCRIPTION OF THE PREFERRED EMBODIMENTS

Figure 1:
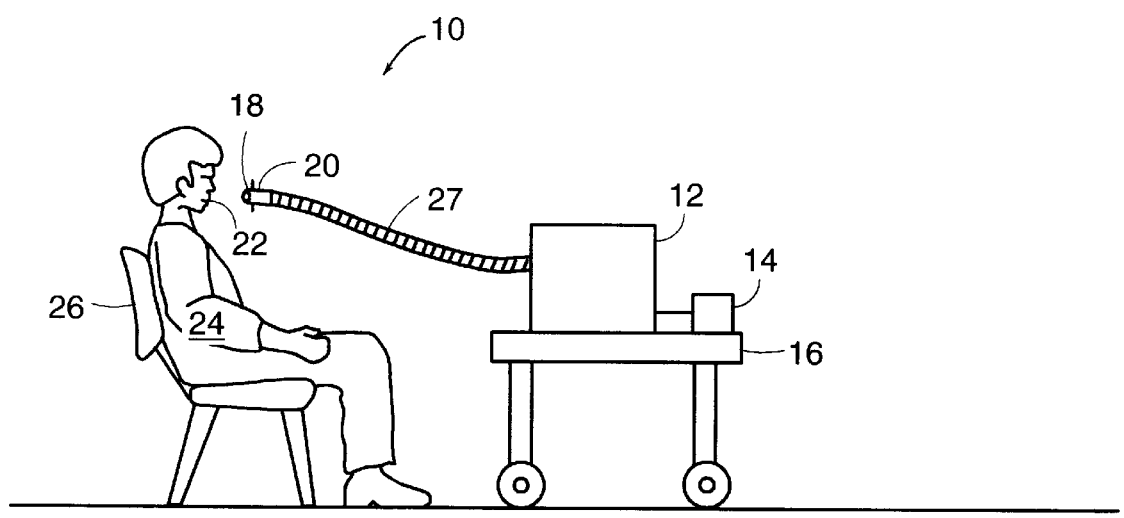
FIG. 1 is a schematic of a system for diagnosing disease in use.

With reference to FIG. 1, a system for detection of cancer, particularly cancerous tumors in a human, or other animal body, includes a vapor sampling device 10, a detector unit 12, and a analyzer unit 14, positioned on cart 16. To diagnose disease from a patient, a vapor sample, in this example a breath sample, is obtained from the patient. The vapor sample is directed to the detector unit 12, which detects and quantifies the presence of sulfur compounds in the vapor sample. As discussed in more detail below, the detector unit detects the sulfur compounds by chemiluminescent reaction with ozone using a process which permits high sensitivity, for example, in the femtogram range, so that the compounds can be detected in the minute quantities often present in biological samples. The analyzer unit is responsive to the detector to report a diagnosis, for example, based on the presence of particular sulfur compound(s) and/or the quantity of the sulfur compound(s).

Analysis of a breath sample or other vapor sample for sulfur compounds is possible because these compounds are produced either as a byproduct of the cancerous metabolic process or of the decay of dying cells, including either or both bacterial and anaerobic decomposition. The sulfur compounds are exhausted by the body from the site of malignancy, through the blood stream to the lungs where they are expelled as part of the exhalent. By highly sensitive analysis, these compounds may be detected and used as indicators for diagnosis.

The sampling device 10 includes a mouthpiece 18, integrally connected to inhaler/exhaler 20, and a hose 27. The mouthpiece is placed in or near the mouth 22 of patient 24, e.g. sitting in chair 26. The patient exhales into mouthpiece 18 thereby providing a sample of his or her breath. The sample is drawn through hose 27, for example, by a light vacuum activated by a pump (not shown), to the detector unit 12. A suitable flow-control process is further described in U.S. Ser. No. 08/813,497, incorporated, supra. Other sampling arrangements can be used, such as adjustment traps for collecting material in the breath, which can be subsequently released into a carrier gas flow by heating.

Figure 2:
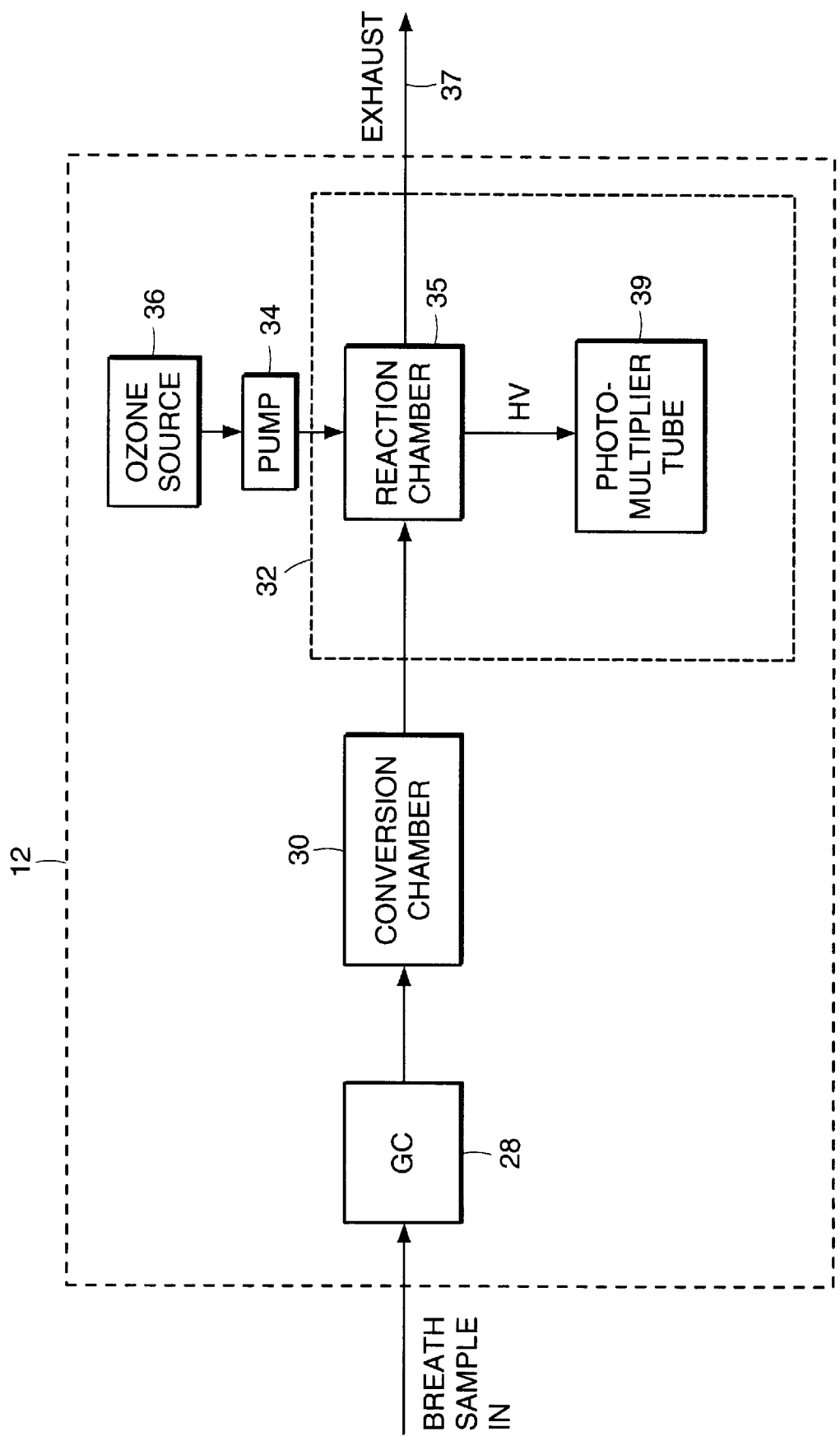
FIG. 2 is a component schematic of the system in FIG. 1.

Referring to FIG. 2, detector unit 12 processes the breath sample to determine the presence of sulfur compounds. Detector unit 12 includes a gas chromatograph (GC) system 28, a conversion chamber 30, and a chemiluminescence detector 32 connected to pump 34 which is employed to pump ozone from an ozone source 36 into chemiluminescence detector 32. The components of detector unit 12, which may be controlled by the analyzer unit 14, are described with reference to FIGS. 3 through 6.

Figure 3:
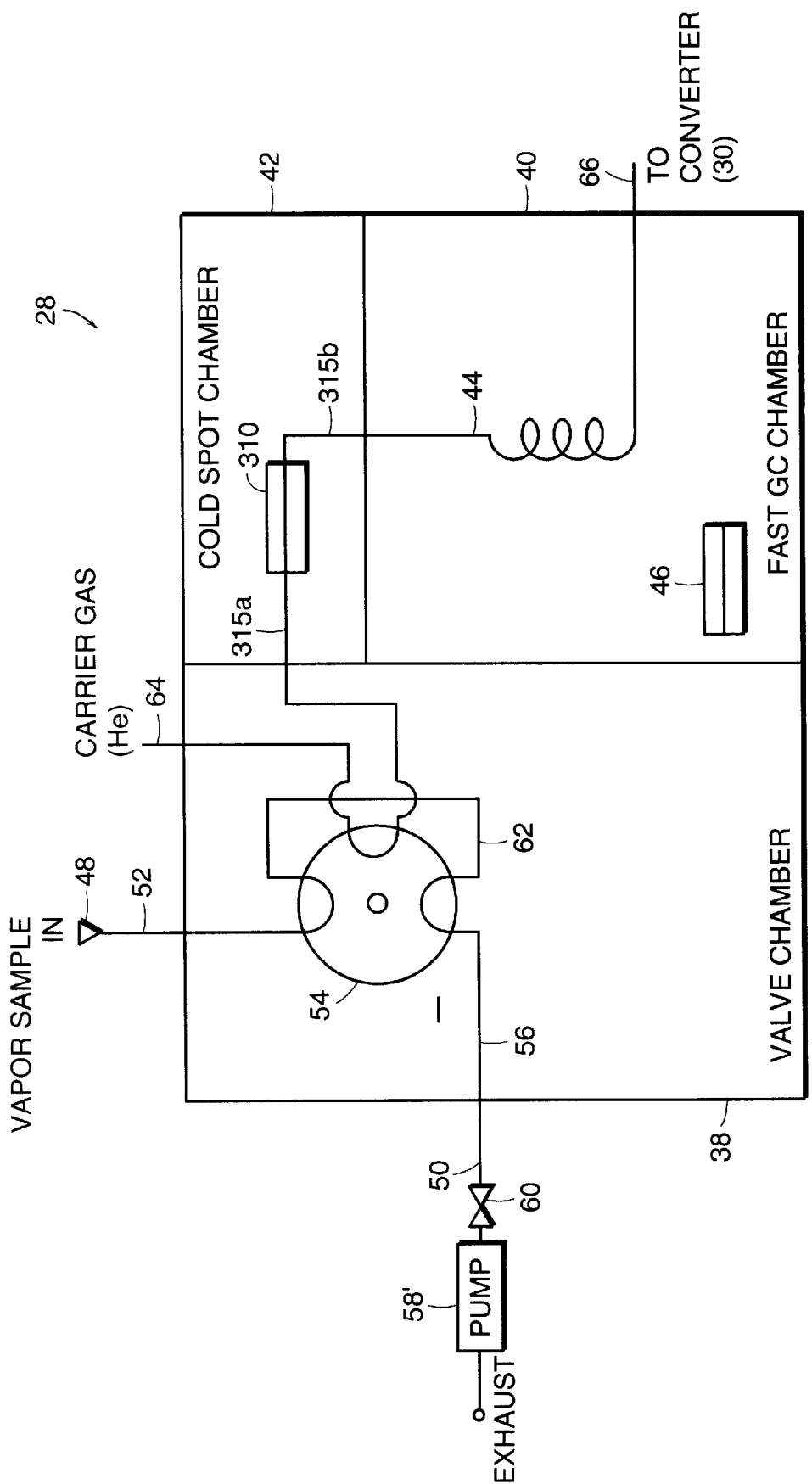
FIG. 3 is component schematic of a gas chromatograph.

Referring to FIG. 3, gas chromatography system 28 includes a valve chamber 38, a fast GC column chamber 40, and a cold spot chamber 42. Column chamber 40 has a column assembly 44 which can be temperature-controlled for rapid heating above ambient temperature and rapid cooling to ambient temperature. Column assembly 44 is a "flash" column assembly which can be heated at high rates, e.g., about 1200° C./min by resistively heating a metal tube closely surrounding the column. The flash GC system is capable of heating at rates greater than 120° C./min over a range of ambient temperature to about 300° C. Most analyses are carried out using heating rates above about 300° C./min.

Figure 4A:
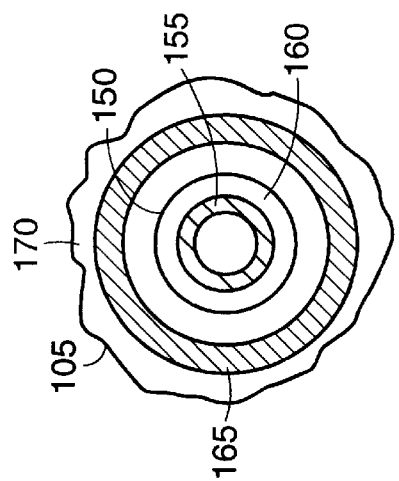
FIG. 4 is a side view of a flash gas chromatography module and FIG. 4a is a cross-sectional view through a segment of the module.
Figure 4:
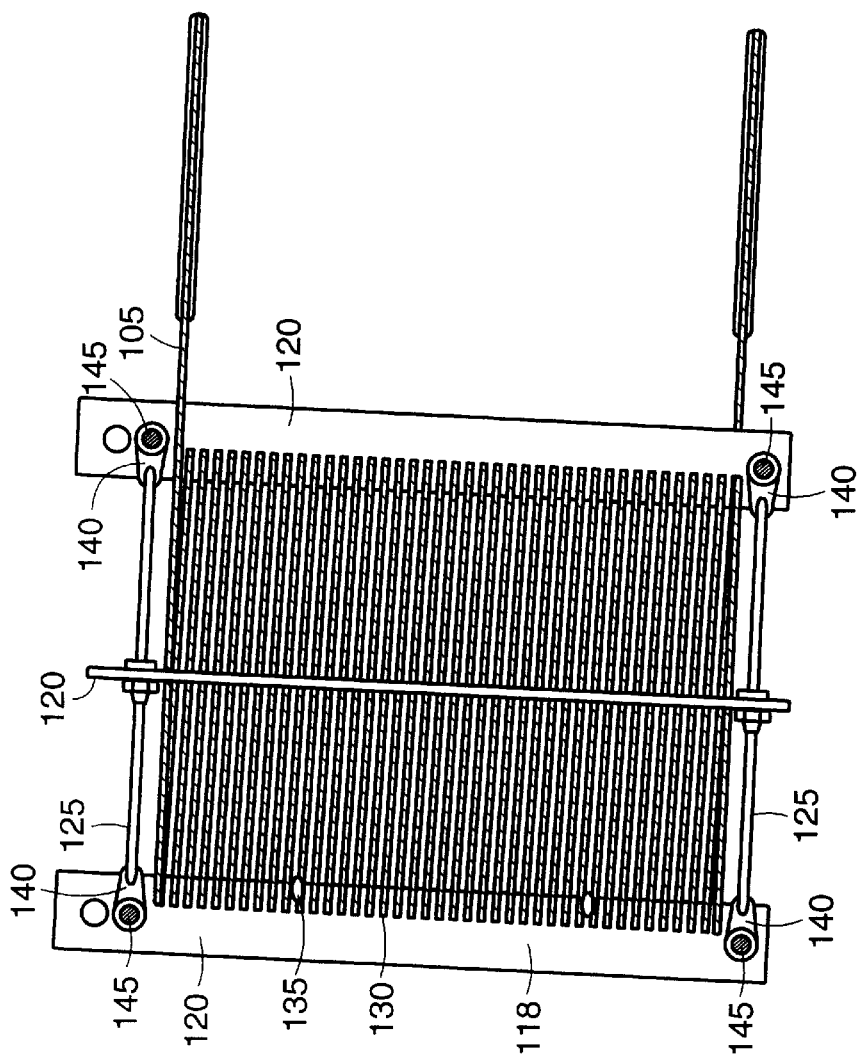

Referring to FIGS. 4 and 4a, the flash column assembly 44 includes a tube 105 arranged in a coil and held in the chamber 40 by a lightweight holder 118. The tube 105 encloses the gas chromatography column 150, which has a layer of polymer 155 coating an interior surface of a glass or quartz fusilic tube 160. The column 150 is located in a stainless steel sheath 165 which may be rapidly heated by application of an electric current. The sheath is located within a electrically insulating glass sleeve 170. To permit insertion of the column 150 into the sheath 165, the outer diameter of the column 150 is smaller than the inner diameter of the sheath 165. The difference between the two diameters must be large enough to permit insertion of the column 150 into the sheath 165 but be small enough to permit rapid heat transfer from the sheath 165 to the column 150. For example, the column may have an outer diameter of about 0.5 mm while the sheath 165 has an inner diameter of 0.55 mm. Column assembly 44 can be rapidly cooled by louver 46 (FIG. 3) which opens the interior of the chamber 40 to a blower (not shown) which directs ambient air into the compartment. Air passes out of the chamber 40 through another set of openings near the top of the chamber (not shown). Further discussion of flash GC arrangements is provided in Rounbehler et al., "High Speed Gas Chromatography," U.S. Pat. No. 5,808,178, issued on Sep. 15, 1998, the entire contents of which is hereby incorporated by reference. A suitable flash GC assembly is available from Thermedics Detection Inc., Chelmsford, Mass.

Referring back to FIG. 3, valve chamber 38 has a sample inlet 48 for receiving a vapor sample and a sample outlet 50 through which gaseous samples can exit the system in a bypass mode in which the sample is diverted from the column, a sample loop 62 for injecting a measured volume of sample, a carrier gas inlet 64 for directing carrier into the system and a rotary valve 54. The sample inlet 48 is adapted to direct the vapor sample into the gas chromatography system the source of sample. It may be useful to draw the vapor sample into the system with a vacuum. The sample outlet 50 includes a line 56 that leads to a pump 58 and includes a valve 60. To receive gaseous sample the pump (e.g., a diaphragm pump operating on the order of a 100 ml/min) draws sample through the inlet line 52, a sample loop 62, and outlet line 56. This avoids creating a back pressure on the sampling system. Just prior to injection of the sample, the valve 60 is operated to expose the sample flow path to atmospheric pressure to equalize the pressure in the sample loop at atmospheric pressure and avoid pressure gradients. Thus, the volume of gas in the sample loop is at atmospheric pressure when it is injected.

The valve chamber 38 also includes a carrier gas inlet 64 for receiving carrier gas to flush the sample onto and through the column. The carrier gas may be, for example, hydrogen, helium, or nitrogen or a mixture of gases such as 40% hydrogen and 60% helium. Valve chamber 38 is heated by air heaters to permit transport of sample through the valve and transfer tubing. Finally, valve chamber 38 has a six-port rotary valve 54 which is actuated to direct flow through the system as described below. The valve may be actuated automatically by a motor driven by signals from the analyzer unit 14.

For sample receiving, valve 54 is positioned (as shown) to direct flow of a vapor sample from the inlet 48 through sample loop 62, (e.g., internal volume of about 500 $\mu$L), and to the outlet 50. It is desirable that the internal diameter of the sample loop is approximately the same as the internal diameter of the transfer tubing leading to a cold spot 310 and column 44. Such a loop can be manufactured from an appropriate length of uncoated capillary GC tubing. Carrier gas flows from the inlet 64 through valve 54 which is positioned to direct the flow to cold spot 310, GC column 44, and through outlet 66 to the converter. To begin analysis, valve 54 is actuated to cut off the supply of sample to the sample loop 62 and direct it to the outlet 50 while at the same time directing a flow of carrier gas through the loop 62. The carrier gas sweeps the sample to cold spot 310 and onto GC column 44.

Figure 5:
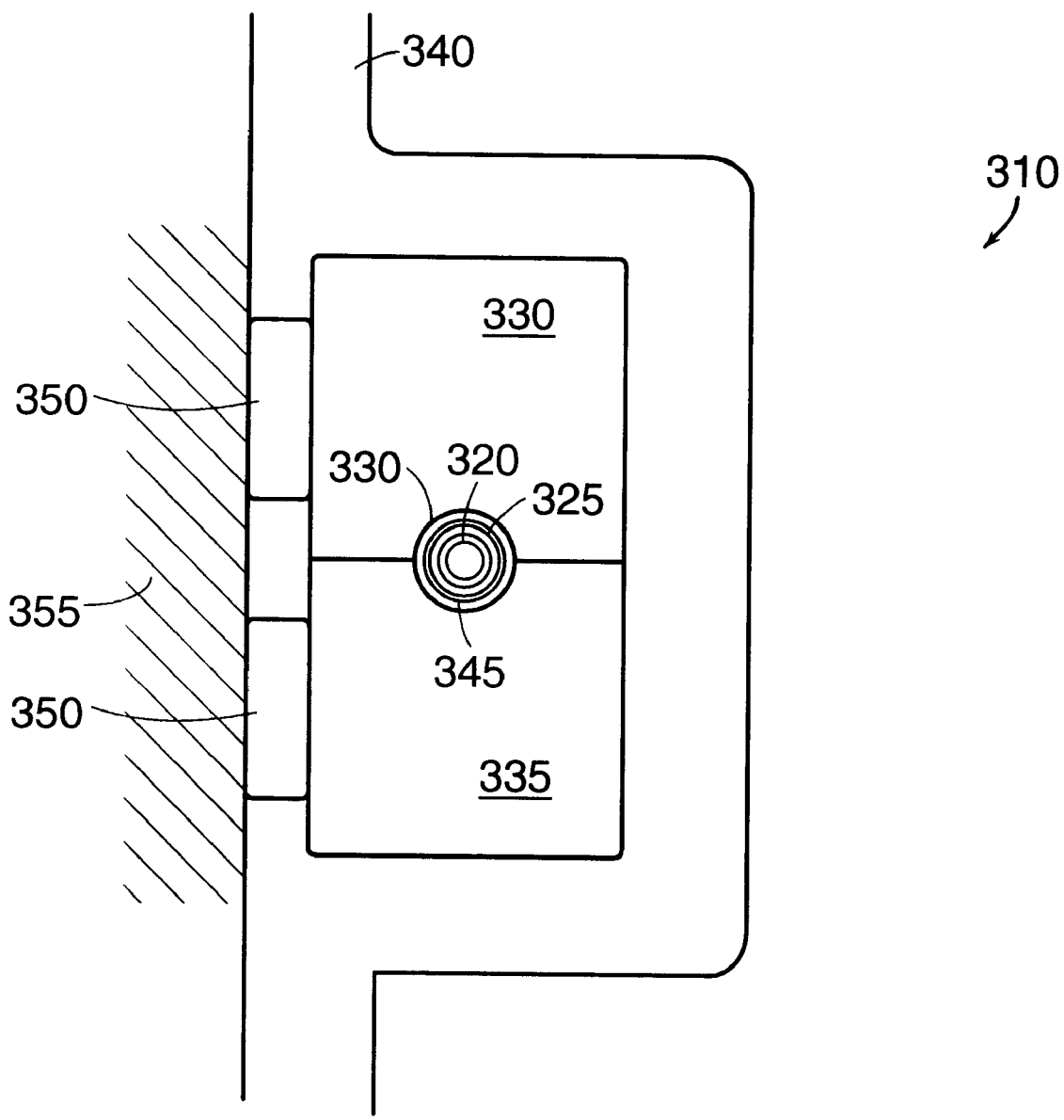
FIG. 5 is an end view showing orientation of a cold spot of the gas chromatography system of FIG. 3.

Further referring to FIG. 5, cold spot 310 (also referred to as a vapor concentrator) is connected to valve 54 and column assembly 44 by a pair of tubes 315a and 315b, respectively. The cold spot 310 is a short gas chromatography column 320 that may be cooled rapidly to concentrate vapors and may be heated rapidly to release the concentrated vapors. Like tube 105, column 320 is surrounded by a metal sheath 325 that may be heated through application of an electrical current.

The column 320 is positioned within a slot 330 in a block 335 of thermally conductive material (e.g., aluminum) that is itself embedded in a rear wall of cold spot chamber 42. A layer of silicone 345 is extruded into the slot 330 to surround the sheath and provide electrical insulation as well as some thermal insulation. The block 335 provides a large thermal mass and maintains the column 320 at a constant temperature when no current is applied to the sheath 325.

The block 335 may be maintained at a low temperature by a pair of Peltier coolers 350. Heat sinks 355 on the exterior of the rear of the valve oven dissipate heat from the Peltier coolers. The Peltier coolers are able to cool the block 335 to a temperature that is about 25° C. less than room temperature, and is essentially independent of the temperature of cold spot chamber 42. Thus, when room temperature is 30° C., the temperature of the block may be maintained at 5° C. Vapors entering the cold spot become entrapped on the polymer coating the interior of the column 320. Compounds are released from the column by rapid heating. Operation of the cold spot is further described in U.S. Pat. No. 5,808,178, incorporated supra.

Figure 6:
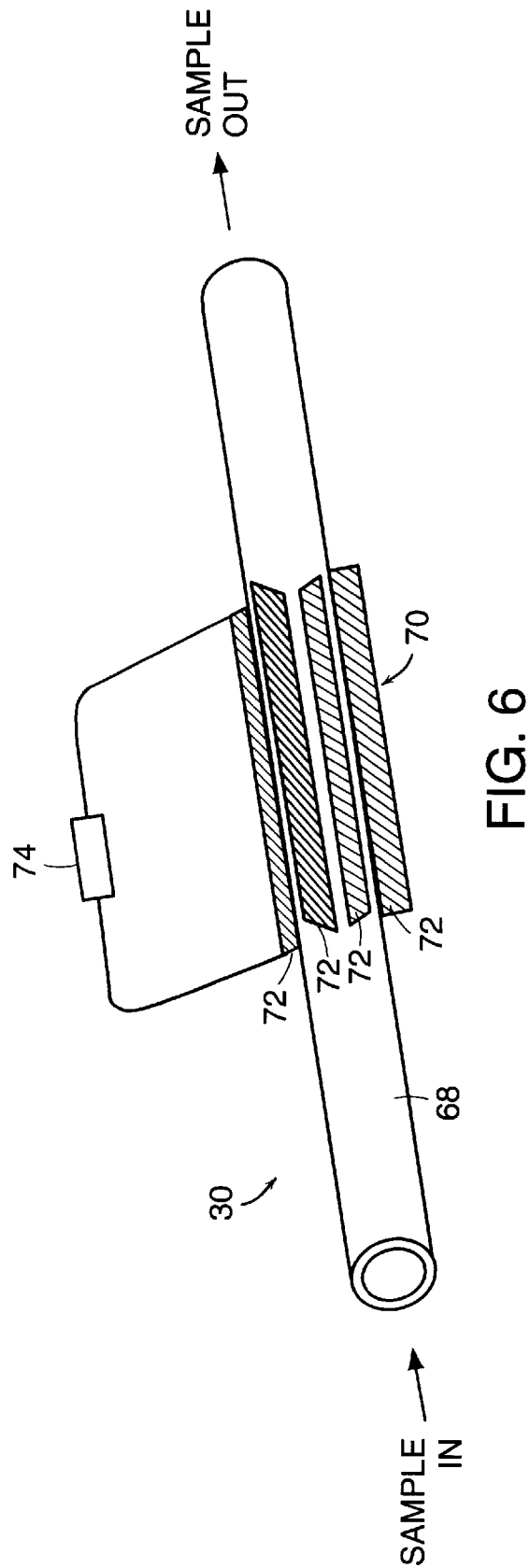
FIG. 6 is a perspective view of a heated-metal conversion chamber.

Referring to FIG. 6, conversion chamber 30 is positioned between GC system 28 and chemiluminescence detector 32. Conversion chamber 30 includes a metal tube 68 heated by an electrical heater 70. The heater 70 is a series (six to eight, four visible) of nichrome-wrapped ceramic rods 72 placed in proximity to the tube 68. The nichrome is connected to an electric power supply 74. A thin electrical insulator may be provided between the rods and the nickel tube. Insulation and an outer covering may be placed over the ceramic rods. The length of the heater is selected to provide a desired length of heated ozone along the tube. The nonheated ends of the tube are used for flow connection. The temperature is maintained at about 200° C. to about 500° C. In other embodiments, the tube 68 is so made of stainless steel. The heating may be achieved by block heaters and controlled by thermocouple feedback arrangement monitored and controlled by the analyzer unit 14. The separated sample from the GC system 28 enters conversion chamber 30 through an inlet orifice and catalytically reacts with the nickel. The byproducts from the reaction are directed through exhaust port 74 to chemiluminescence detector 32.

The conversion chamber enhances the sensitivity of the measurement. The improved sensitivity is due to conversion of sulfur compounds which are present in biological matter to reactive organic sulfur species but without complete reduction to $H_2S$ or SO. For example, methyl mercaptan may undergo the following conversion reaction:

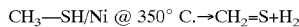

$$CH_3\text{—}SH/Ni @ 350° C. \rightarrow CH_2=S+H_2$$

The resulting double-bonded sulfur compound is highly reactive. When it is exposed to ozone, intense luminescence results. Three luminescence reactions may occur: 1) Ozone reacts directly with the sulfur in the compound. 2) Ozone reacts across the double bond. 3) The two reactions 1) and 2) yield SO which also reacts with ozone thereby resulting in a third luminescence pathway.

Referring to back FIG. 2, chemiluminescence detector 32 includes a reaction chamber 35 having an inlet connected to pump 34 and an outlet 37. In chamber 35, the sample from conversion chamber 30 reacts with ozone, supplied by ozone source 36 and pumped in by pump 34, and produces a chemical species which emits radiant energy. The radiant energy is detected by photomultiplier tube 39 after the radiant energy passes through a quartz filter (not shown) that permits radiant energy having wavelengths greater than about 190 nanometers to pass. The photomultiplier tube produces an electrical signal that is proportional to the radiant energy incident thereon. This signal is further processed by analyzer unit 14. The chemiluminescence detector operates in a manner similar to a standard chemiluminescence detector with the exception that the quartz filter passes a wider range of wavelengths than the filters of standard detectors, which are configured to detect primarily infrared energy and typically pass radiant energy having wavelengths greater than 600 nanometers. By passing a wider range of wavelengths, the quartz filter permits the photomultiplier tube to also detect radiant energy having wavelengths less than 600 nanometers (e.g., 300 to 500 nanometers), which are typical of sulfur-containing compounds. For example, when dimethyl disulfide, methyl mercaptan, hydrogen sulfide, dimethyl sulfide and sulfur dioxide (sulfur compounds that are indicators of tumors) are reacted with ozone, radiant energy having wavelengths in the range from 300 to 500 nanometers is produced. To limit detection to primarily sulfur compounds, a bandpass filter that passes wavelengths in the 300 to 500 or, preferably, 300 to 400 nanometer ranges can be substituted for the quartz filter. Filters are commercially available, for example, Corning 5-56 or 5-61, available from Oriel Corp., Stratford, Conn.

The control of the pressure in the reaction chamber contributes to the high sensitivity of sulfur compound analysis. The pressure is held at a relatively high level which produces the dual benefit of quenching luminescence (believed due to three body reactions) from nonsulfur compounds, e.g., hydrocarbon and NO compounds, while enhancing the signal from the sulfur compounds. The pressure is preferably in the range of about 0.25 to 3 Atm, e.g., about 0.5 Atm. To achieve this pressure, a pump (for example, diaphragm pump, Model UN05 ATI, available from KNF Neuberger Inc., Trenton, N.J.) is used between the ozone generator and the chamber. In a system such as that illustrated in FIG. 2, in which the sample is introduced from a GC, a pump for the sample is generally not needed. However, in systems where the sample is introduced directly into the chamber, a pump may be used.

Referring back to FIG. 1, analyzer unit 14 is a microprocessor-based or hard-wired controller for programming the various operations of detector unit 12. Analyzer unit 14 quantifies the electrical signals from detector unit 12 related to chemical composition of the vapor sample.

Operation

Figure 7:
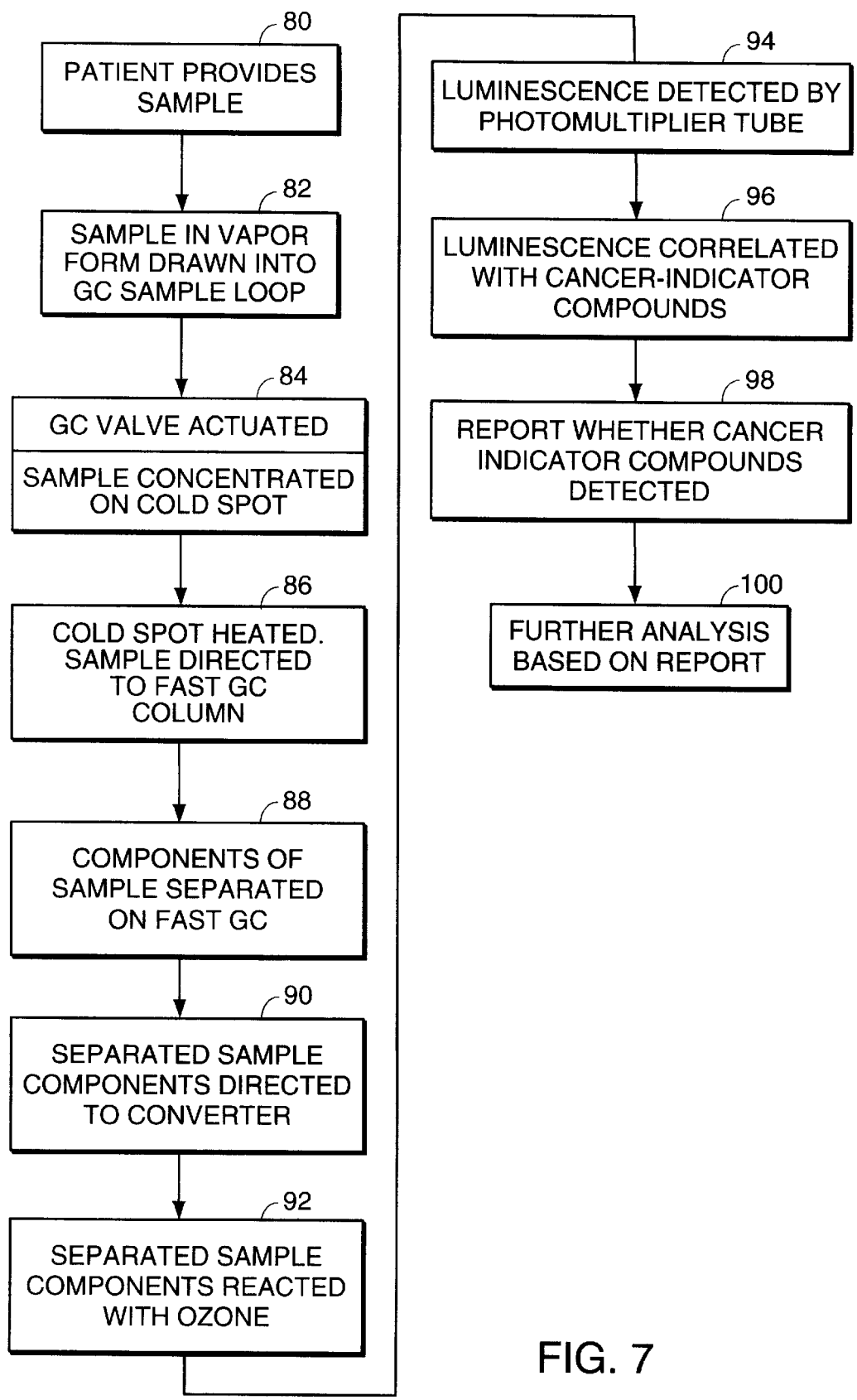
FIG. 7 is a flow diagram of an analysis of a vapor sample using the system described in FIG. 2.

Referring to FIG. 7, a flow chart illustrates how a vapor sample may be analyzed on the system described above. In the first step 80, the patient exhales into inhaler/exhaler 20 thereby providing a breath sample. In step 82, the sample in vapor form is drawn into the GC sample loop 62. Valve 54 is positioned to cause flow from the sample inlet 48 through sample loop 62 and out sample outlet 50. In the next step 84, valve 54 is actuated to direct carrier gas from inlet 64 through sample loop 62 to sweep the sample to cold spot 310, where the sample becomes concentrated. As indicated in step 86, cold spot 310 is heated which causes the sample to be released from cold spot 310 and directed to column 44. In the next step 88, the components of the vapor sample are separated in the fast GC column.

In step 90, the separated sample is directed to conversion chamber 30 where the sample undergoes catalytic reaction. Next, the products of the catalytic reaction are directed to chemiluminescence detector 32.

In the next step 92, the sample components react with ozone in the reaction chamber 35 of chemiluminescence detector 32, the ozone from source 36 being pumped into reaction chamber 35 by pump 34. Luminescence is detected by photomultiplier tube 39, as indicated by step 94. To increase the sensitivity of chemiluminescence detector 32, pump 34 is further employed to pressurize reaction chamber 35.

In step 96, the electrical signal related to the detected luminescence is correlated with cancer-indicator compounds by analyzer unit 14. Finally, in step 98, analyzer unit 14 reports whether cancer-indicator compounds have been detected.

In step 100, further analysis may be carried out with another technique, such as gas chromatography/mass spectrometry (GC/MS) or mass spectrometry/mass spectrometry (MS/MS) to, for example, increase the specificity of the chemical analysis. In the further analysis, the sample or patient may be treated to provide higher sulfur compound concentrations which may be needed for a less sensitive analytical method.

Further Embodiments

Further embodiments may include, for example, systems arranged for vapor samples from various biological sources, and diagnosis of different diseases. For example, the system may be arranged to take an out-gas vapor sample from excised tissue taken as part of a biopsy operation. Body fluids, for example blood, and body waste such as feces can also yield vapor samples detectable by the system. The vapor sample may be excreted from the skin. The vapor sample may be obtained from plant sources. The biological source may also be treated prior to vapor sampling, for example by chemical fixing, tissue differentiation techniques such as centerfugation or freezing. The vapor sample can be a readily vaporizable sample, such as liquids which might be heated to a vapor without destroying the integrity of the sulfur indicators. In the case of sampling liquids, a volatizer is used to vaporize the liquid sample to a gas which is then analyzed for its chemical composition. The volatilizer may be a GC. In a particular embodiment, an incision is made in the patient and a sampling probe is placed in the area of interest within the body for sampling of either gases or liquids.

The analysis may be arranged to diagnose infections, precancerous conditions or diseases generally in which tissue decay is present. For example, damage to the intestine may be detected. The breath analyzer in certain embodiments can be used to detect infections, or it can also be used to detect and determine the origin of bad breath in a patient. Other diseases that can be detected include ulcers, viral infections, bacterial infections, liver diseases (e.g. hepatitis and cirrhosis), internal body infections, and heart disease. Differentiation of bacterial infections from autolytic decomposition can be determined by analysis of the type of sulfur compounds. For example, bacterial decomposition is indicated by a relatively high concentration of dimethyl disulfide and autolytic decomposition is indicated by a relatively high concentration of methyl mercaptan.

While the high sensitivity of the techniques described above permit analysis of out-gas samples or other neutral vapors, the sample, biological matter or patient may also be treated to increase the concentration of sulfur compounds. For example, a sulfur compound inducing treatment may be provided to the sample (e.g. a sample preconcentrator) or a dietary supplement supplied to the patient. Concentration of the sample may be useful when a less sensitive analysis (e.g. by MS/MS, GC/MS or infrared analysis) of the sample is performed for detecting specific sulfur compounds. Alternatively, the patient may be deprived of foods containing or metabolizing to sulfur compounds so that only sulfur compounds produced by the body are detected.

In other instances, other detection schemes may be used, such as lead azide paper tapes, flame photometric detectors, and labelled monoclonal antibodies. Where such techniques can achieve sensitivity in the femtogram range, they may be used in place of chemiluminescence. In cases where the sensitivity is not sufficient, the tissue may be pretreated or the sample preconcentrated.

Example

The following combination of conversion chamber and reaction chamber parameters may be used to enhance the sensitivity of the sulfur detection measurement.

| Conversion Chamber | |
|---|---|
| Metal: | Nickel |
| Outer Diameter: | 1/16" |
| Inner Diameter: | less than about 0.040 inch |
| Overall Length: | 12" |
| Heater (six nichrome-wrapped ceramic rods) | 3" long |
| Operating Temperature: | 300–350 ± 4° C. |
| Supplemental Oxygen Flow: | at 10% of carrier flow rate |

Preferably, the conversion chamber is a nickel tube with an inner diameter approximately the inner diameter of the GC column to provide good flow characteristics. The nickel tube is heated over only a portion of its overall length, typically in the central region. The ends of the tube are adapted with compression fittings to allow plumbing to GC columns and tubing. The heated length is preferably about 3 inches and the overall length is about 12 inches. The length of the heated portion is selected to provide an optimal residence time of the sample with the heated nickel. The heater may be implemented as a series of nichrome wrapped ceramic rods placed in proximity to the nickel tube and separated by a thin layer of insulating material. The temperature is held at about 300 to 350° C. and is monitored by a thermocouple. Preferably, a flow of supplemental oxygen is provided into the chamber, along with the carrier gas, using a t-fitting just upstream of the tube. The oxygen enhances sensitivity by regenerating the catalytic surfaces of the nickel or participating in the conversion reaction.

| Luminescent Reaction Chamber | |
| --- | --- |
| Volume: | 0.5–1.5 ml |
| Narrow Band Pass Notch Filler | 340–400 nm |
| Pressure in Chamber: | 0.25–2 atm |
| Flow Rate through Chamber: | 1–5 ml/min (compatible with GC flow rate) |
| Temperature: | 23–300° C. |
| PMT: | Photocathode with max sensitivity around 340/400 nm |

The reaction chamber is a mirror-polished cup-shaped (concave) optical chamber including an inlet for ozone, an inlet for sample and an outlet of the reaction product. The volume of the chamber is preferably kept small, e.g., around 0.5 ml. Because of the rate of the sulfur reactions, sensitivity is enhanced by mixing the ozone and sample only after they have reached the chamber and by keeping the chamber volume low, e.g., around 0.5 ml. The pressure of the chamber is relatively high which provides a dual benefit of an environment of high ozone concentration, promoting reaction with sulfur, and in addition, quenches competing reactions. Operating at high pressure provides, e.g., factor of 10 improvement in sensitivity over lower pressure environments, e.g., 50 torr. At these higher pressures, the flow rate through the chamber may be compatible with GC flow rates, e.g., around 1–5 ml/min. Sensitivity can also be enhanced by use of a narrow band notch filter and a PMT with optimum sensitivity in the sulfur luminescence range. The temperature is maintained sufficient to avoid residue buildup on the interior surfaces.

Still other embodiments are within the following claims. What is claimed is:

1. A method of assisting diagnoses of disease in biological matter, comprising:
    obtaining a vapor sample from said biological matter, analyzing the vapor sample by luminescent reaction with ozone for the presence of sulfur compounds in a concentration range of about 500 femtograms or less, and assisting diagnoses of disease based on said analyzing.

2. The method of claim 1, comprising processing said sample by gas chromatography prior to said analyzing.

3. The method of claim 2 comprising reporting the presence or absence of disease based on a profile of particular sulfur compounds.

4. The method of claim 3 comprising assisting diagnoses of the presence or absence of disease based on the profile of dimethyl disulfide, methyl mercaptan, hydrogen sulfide, dimethyl sulfide or sulfur dioxide.

5. The method of claim 1 further comprising detecting said sulfur compounds in a concentration range of about 25 femtograms or less.

6. The method of claim 1 comprising quantifying said sulfur compounds.

7. The method of claim 1, wherein said vapor sample is exposed to a pressure between about 0.5 atm to about 3 atm after obtaining said sample.

8. A method of detecting a sulfur compound from biological matter, comprising:
    obtaining a vapor sample containing a sulfur compound from biological matter,
    treating said vapor sample by exposing the sulfur compound in said vapor sample to a heated metal, without added reducing agent,
    exposing said treated sample to ozone,
    detecting luminescence generated by exposing said treated sample to ozone, and
    analyzing said luminescence to determine the presence of said sulfur compound.

9. The method of claim 8 wherein said metal is heated to about 350° C.

10. The method of claim 8 or 9 wherein said metal comprises nickel or stainless steel.

11. The method of claim 8 or 9 comprising pretreating said vapor sample by separating compounds in said sample.

12. The method of claim 11 comprising pretreating said vapor sample, by gas chromatography.

13. The method of claim 8 or 9 comprising obtaining said vapor sample by collecting vapor from an animal body.

14. The method of claim 13 comprising heating the body to aid release of vapor.

15. The method of claim 8 or 9 wherein said sulfur compound is selected from the group consisting of methyl mercaptan, dimethyl sulfide and dimethyl disulfide.

16. The method of claim 8 or 9 comprising analyzing said luminescence to determine the amount of sulfur compound in said vapor sample.

17. The method of claim 8 or 9 comprising exposing said vapor sample to a heated metal in the presence of air.

18. The method of claims 1, 3, 5, or 8, comprising treating said vapor sample prior to luminescent reaction with ozone by converting sulfur compounds to reactive species without complete reduction to $H_2S$ or SO.

19. The method of claim 18 wherein said conversion of said sulfur compounds is by exposure to a heated metal, without added reducing agent.

20. The method of claim 19 wherein the metal is stainless steel or nickel.

* * * * *